United States Patent [19]

Diepers et al.

[11] 4,354,388
[45] Oct. 19, 1982

[54] METHOD FOR NONDESTRUCTIVE MATERIAL TESTING WITH ULTRASOUND PULSES

[75] Inventors: Heinrich Diepers, Höchstadt; Joachim Niewisch, Nuremburg, both of Fed. Rep. of Germany

[73] Assignee: Siemens Aktiengesellschaft, Munich, Fed. Rep. of Germany

[21] Appl. No.: 160,330

[22] Filed: Jun. 17, 1980

[30] Foreign Application Priority Data

Jun. 28, 1979 [DE] Fed. Rep. of Germany ....... 2926173

[51] Int. Cl.³ ............................................. G01N 29/04
[52] U.S. Cl. ......................................... 73/612; 73/628
[58] Field of Search ................. 73/612, 614, 615, 628, 73/625

[56] References Cited

U.S. PATENT DOCUMENTS 3,683,680  8/1972  Johnson et al. ........................ 73/628
4,012,952  3/1977  Dury ..................................... 73/612
4,173,007  10/1979 McKeighen et al. .................. 73/625

FOREIGN PATENT DOCUMENTS 1698518  3/1972  Fed. Rep. of Germany .
2600720  7/1976  Fed. Rep. of Germany .

*Primary Examiner*—Anthony V. Ciarlante
*Attorney, Agent, or Firm*—Kenyon & Kenyon

[57] ABSTRACT

A method for ultrasonic fault localization, in which the fault is determined from the travel time of the ultrasound pulses and the echo pulses, in which an echo pulse reflected in the workpiece at a fault is received at three different points on the surface, the electronic echo pulses are electronically added in phase with a delay dependent on the different propagation times, and fed to an electronic time window such that during the open time of the time window, only echo pulses from the fault are picked up. The fault is displayed graphically as to size, position and shape.

11 Claims, 5 Drawing Figures

METHOD FOR NONDESTRUCTIVE MATERIAL TESTING WITH ULTRASOUND PULSES

BACKGROUND OF THE INVENTION

This invention relates to a method for nondestructive material testing with ultrasound pulses which are introduced into the work piece under test and are reflected by a fault, the position of which is derived from the propagation time of the ultrasound pulses and the echo pulses.

In nondestructive material testing, methods which are based on the scattering or reflection of ultrasound waves in materials and which allow the detection and localization of changes in the structure, especially of faults are already known. Ultrasound is directionally coupled into the surface of the workpiece under test and is displaced on the surface along the workpiece under insonification conditions which remain constant. The echo scatter radiation from the workpiece is picked up and the amplitude of the successive echo pulses is made visible on a picture screen. During the spatial displacement, the amplitude changes of the echo pulses resulting from the different successive ultrasound pulses are recorded or stored. On the picture screen, the amplitude of the echo pulses can be made visible as a function of the lengthwise displacement of the ray bundle. In the arrangement for implementing the method, the transmitters for the ultrasound pulses can, at the same time, be used as receivers for the echo pulses. (German Offenlegungsschrift No. 2 600 720).

In another method for the continuous testing of solid bodies by means of ultrasound, the workpiece is immersed in a liquid coupling medium and the result of the test is likewise displayed by means of a cathode ray tube having brightness modulation. To take into consideration the influence of propagation paths of different lengths for the ultrasound pulses in a coupling medium on the one hand and in the workpiece on the other hand, the time interval between the emission of an ultrasound pulse and its arrival at a point of incidence of the body under test is determined by means of an echo signal assigned to this point of incidence (German Offenlegungsschrift No. 16 98 518). However, testing of relatively large work pieces requires a correspondingly large expenditure. To this disadvantage is added the fact that all liquid coupling media generally have a substantially lower acoustic impedance than the material under test.

The coupling becomes particularly difficult if numerous transducer elements are combined in a so-called array. Therefore, materials testing is limited to small arrays with, say, 20 oscillators. In a sector manner, focusing and sluing can be obtained by phase-shifted steering, so that a certain angular range can be scanned. However, even with the sector scanner it is only possible to generate a cross-sectional picture, i.e., a two-dimensional picture. Large arrays are impossible because of the coupling problems to predetermined curved surfaces.

It is now an object of the present invention to describe a method for nondestructive material testing with ultrasound which allows finding a fault and imaging it, in addition, three-dimensionally in a relatively large volume, approximately $0.5 \times 0.5 \times 0.5$ m$^3$, nearly independently of the surface structure and form. Finding and imaging the fault should be possible in a short time, preferably substantially less than one minute.

SUMMARY OF THE INVENTION

According to the present invention, this problem is solved in a method of the above-mentioned kind by feeding at least one ultrasound pulse to the fault location from the surface of the workpiece; picking up the echo pulse at three different points of the surface; converting the echo pulse into electronic echo signals; adding these echo signals, superimposed in phase according to their different propagation times, electronically and feeding the resulting sum to a memory via an electronic time window. The propagation time depends on the coordinates of the fault and the sound velocity in the material of the workpiece.

The volume elements are insonified successively and the reflected signals are picked up with ultrasonic transducers arranged at predetermined points on the surface, and are added with the correct phase. By an electronic time window, the opening instant of which is a function of the coordinates of the volume element, and the width of which is a function of the size of the volume elements, together with the delays of the transmitter and echo pulses, a volume element is defined as to location and size. A fault in this volume element manifests itself by an enlarged amplitude of the summed signal in the time window. The value of this amplitude is stored in an electronic memory after analog-to-digital conversion. The method permits imaging the workpiece three-dimensionally without changing the position of the ultrasonic transducers during the entire scanning of the predetermined volume which is determined as to shape and size by the choice of the propagation times of the ultrasonic transmitting and echo pulses. The determined fault location is imaged as to size, position and shape within the scanned volume.

Ultrasound pulses can be supplied to the fault from three points arranged at a given distance from each other on the surface with a time interval such that they are reflected at the fault simultaneously. The echo pulse is then received again at the points of the insonification with correspondingly different time spacings, and is processed electronically. The superposition of the echo signals with the correct phase is accomplished by electronic delay stages, the delay times of which are the same ones as in transmitting. After addition, they appear in the time window, the opening time of which is chosen so that the echo signals can be reflected only by a predetermined volume element of the workpiece, if the latter contains a fault. The volume element is determined unequivocally by the delay times and by the window opening instant. The window opening time duration determines the magnitude of the volume element.

After A/D conversion, these signals are fed to a memory. An image of the memory content can then be displayed on a picture screen, preferably in perspective. The three ultrasonic transducers are coupled, for this purpose, only once to defined points and must not be moved during the scanning period. Since three points always define a plane, only the absolute distances of the ultrasonic transducers still enter into the coordinate calculation.

In one arrangement for implementing the method, a transmitter and three receivers are arranged on the surface of the workpiece at a predetermined distance from each other. The transmitter is connected to an electronic pulse generator, which opens the electronic time window via an electronic delay stage. Associated with the receivers are respective electronic delay stages, the delay times of which are chosen so that according to the propagation time of the transmitter pulse and the propagation time of the echo pulse to the different receivers, the electronically added echo signals can be reflected only from a predetermined volume element of the workpiece. This volume element contains a fault if echo signals are registered in the time window. The electronic addition is accomplished in a summing amplifier which is followed by the electronic time window.

In another particularly advantageous arrangement for implementing the method, three ultrasonic transducers which serve at the same time as transmitters for the ultrasonic pulses and as receivers for the echo pulses are used these can preferably be piezoelectric oscillators. The channels associated with the transducers each contain an electronic double-throw switch, in addition to the electronic delay stages. In one position, this double-throw switch transmits the transmitter pulse from a pulse transmitter via the delay stages to the transducers. It is then switched over and subsequently transmits the echo signals picked up by the transducers via the same delay stages and the electronic summing amplifier to the time window.

Because of the relatively complicated interrelation between coordinates and propagation times, all switching functions are controlled by an electronic computer. A microprocessor is advantageously provided as the computer. Into the computer the coordinates of the different volume elements to be scanned, are set, in accordance with a freely selectable scheme. From these coordinates, the computer calculates the required delay times for the delay stages and, in the embodiment of the fault localization system with three ultrasonic transducers as transmitters and receivers, controls the switching of the channels after the transmitter pulses are transmitted and the opening of the time window at an instant which is a function of the coordinates of the volume element.

A storage cell is associated with each volume element. The memory can be filled in any desired sequence. To find a fault, it may be desirable to scan the volume first coarsely in a correspondingly short time by making the volume elements relatively large. As soon as a fault is determined with this coarse scanning, the immediate surroundings of the fault can be scanned by making the insonified volume elements smaller and thus, the form, size and location of the fault can be determined. A magnifier effect is obtained by this coarse and fine scanning. Since the memory contains three-dimensional information, any desired presentation of the fault can be chosen, preferably in perspective.

The sensitivity of the system can be further increased substantially if sector scanners are used which permit a sluing in three dimensions instead of the three ultrasonic transducers.

DETAILED DESCRIPTION OF THE INVENTION

Figure 1:
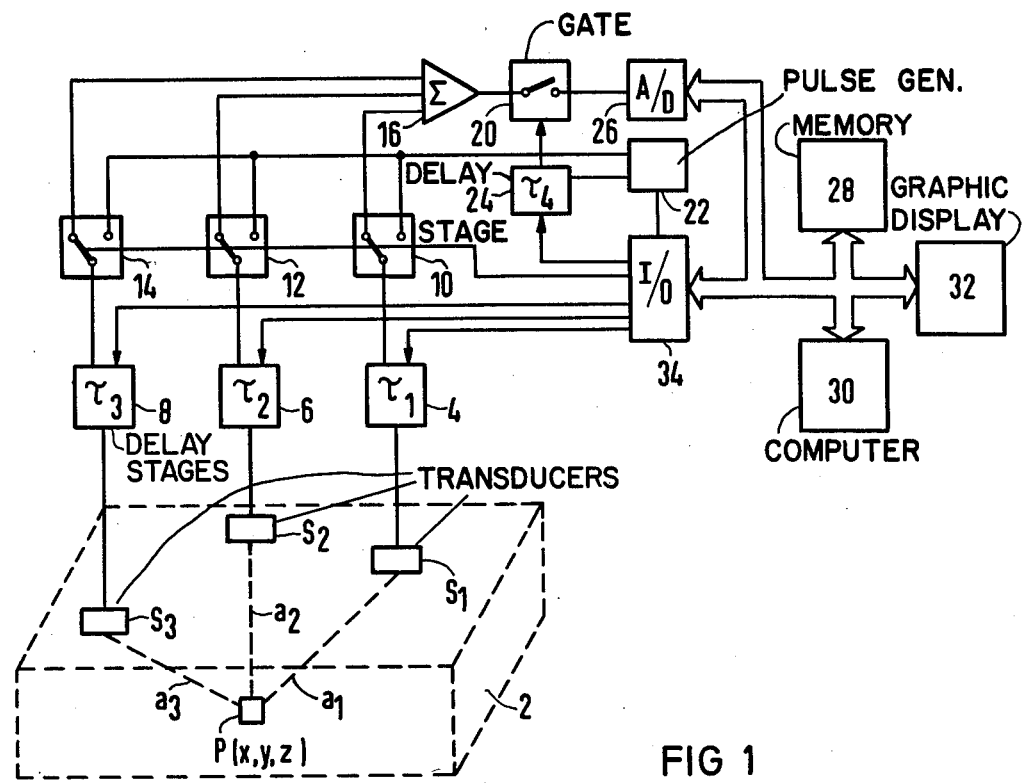
FIG. 1 is a schematic block diagram of an and arrangement for implementing the method of the present invention.

According to FIG. 1, three ultrasonic transducers $S_1$, $S_2$, and $S_3$ are arranged on the surface of a workpiece 2. The transducers serve simultaneously as transmitters for an ultrasonic pulse and as receivers for an echo pulse reflected at a fault located at point P (x, y, z) in the volume of the workpiece 2, where x, y, and z are Cartesian coordinates. The ultrasonic transducers, $S_1$ to $S_3$ may, for instance, be piezoelectric crystal oscillators with a spherical characteristic. The ultrasonic transducers $S_1$ to $S_3$ are arranged at predetermined mutual distances, not specifically designated in the figure, on the surface of the workpiece 2. The ultrasonic transducers $S_1$ to $S_3$ have predetermined distances $a_1$, $a_2$ and $a_3$, respectively, from a volume element of the workpiece 2, which is assumed to contain a fault, at a point P. The ultrasonic transducers $S_1$ to $S_3$ are each connected via an electronic channel containing respective delay stages 4, 6 and 8 and via a summing amplifier 16 to an analog gate 20 which serves as a time window. The delay times of the delay stages 4, 6 and 8 are dependent on the coordinates x, y, and z of the point P and the propagation time of the ultrasound pulses $U_S$ in the workpiece 2. In addition, the channels each contain an electronic double-throw switch, 10, 12 and 14, respectively, which connect the ultrasonic transducers $S_1$ to $S_3$ to an electronic pulse generator 22. In one switch position of the double-throw switches 10 to 14, pulse generator 22 addresses, via the delay stages 4 to 8, the ultrasonic transducers $S_1$ to $S_3$ and, in addition, via an electronic delay stage 24, the gate 20. The output signals of the gate 20 are preferably fed to a memory via an analog-to-digital converter 26. The delay stages 4, 6, and 8 as well as 24 are connected to an electronic computer 30. According to its program, the computer 30 sets the coordinates x, y, and z of the point P, and after the transmitter pulses $U_S$ are delivered, also controls the switching over of the double-throw switches 10, 12, and 14 as well as, via the delay stage 24, the opening instant of the gate 20, which depends on the coordinates x, y and z of the point P and on the propagation time of the ultrasound pulses in the workpiece 2.

Figure 2:
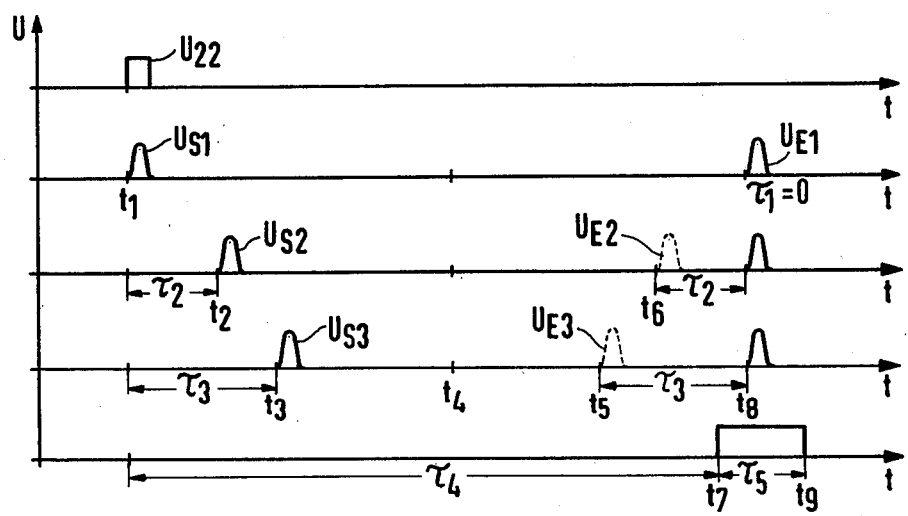
FIG. 2 is a diagram showing the operation of the arrangement of FIG. 1.

In the diagram according to FIG. 2, different signals U of the arrangement according to FIG. 1 as well as the ultrasound pulses and the echo signals are plotted as a function of the time t. At the time $t_1$, the pulse generator 22 is to deliver, for instance, a pulse $U_{22}$, which is fed via the double-throw switch 10 and the delay stage 4 to the ultrasound transducer $S_1$ and triggers there an ultrasound pulse $U_{S1}$ with a delay of $\tau_1 = 0$, i.e. without delay. The pulse $U_{22}$ is also fed via the double-throw switch 12 and the delay stage 6 to the ultrasonic transducer $S_2$. The delay stage 6 is set so that an ultrasound pulse $U_{S2}$ is triggered by the ultrasonic transducer $S_2$ only with a delay $\tau_2$ at the time $t_2$. In the same manner, the pulse $U_{22}$ is fed to the ultrasonic transducer $S_3$ via the double-throw switch 14 and the delay stage 8 with a delay $\tau_3$ to produce an ultrasound pulse $U_{S3}$ at the time $t_3$. The delay $\tau_2$ of the ultrasound pulse $U_{S2}$ caused by the delay stage 6 is chosen in accordance with the small distance of the ultrasonic transducer $S_2$ from point P and the propagation time of the ultrasound pulse $U_{S2}$ in the workpiece 2. The delay of the ultrasonic transducer $S_3$, because of its larger distance from point P, is chosen accordingly longer. At the same time, the delay stage 24 is employed to delay the pulse $U_{22}$, so as to open the gate 20 after a delay $\tau_4$ at the time $t_7$. After the ultrasound pulse $U_{S3}$ is delivered at the time $t_3$, the double-throw switches 10, 12 and 14 are switched over by the computer 30 via an I/O interface 34.

The ultrasound pulse $U_{S1}$ of the transmitter $S_1$ which is farthest removed from the point P has the longest travel time. The time $t_7$ of opening the gate 20 is chosen so that the echo pulse $U_{E1}$ which is reflected from the point P and arrives via the delay stage 4 and the double-throw switch 10 as well as the summing amplifier 16 with a delay $\tau_1 = 0$, appears at the gate 20 at a time $t_8$, when the window is open. According to the shorter distance $a_2$, the ultrasound pulse $U_{S2}$ is reflected earlier and would arrive at the gate 20 at the time $t_6$, as indicated in the figure by the dashed lines. However, it is fed by the delay stage 6 with the same delay $\tau_2$ as in the transmitted case via the double-throw switch 12 and the summing amplifier 16 to the gate 20 and appears there accordingly in the time window at the time $t_8$. In the same manner, the echo pulse $U_{E3}$ is fed to the gate 20 after its arrival at the ultrasonic transducer $S_3$ at the time $t_5$, through the delay stage 8 with the delay $\tau_3$ via the double-throw switch 14, where it appears in the time window at the time $t_8$. On the picture screen 32, the position of the point P is determined by the coordinates x, y, z which are set into the computer 30 by the program and at which the computer calculates the delay times $\tau_1$ to $\tau_3$ as well as $\tau_4$, and controls the switching of the double-throw switches 10 to 14. Since a fault is assumed at point P, the corresponding position on the screen will be brighter. The open time $\tau_5$ of the time window determines the size of the individual volume elements and thereby, the resolution of the reflector localization system.

Figure 3:
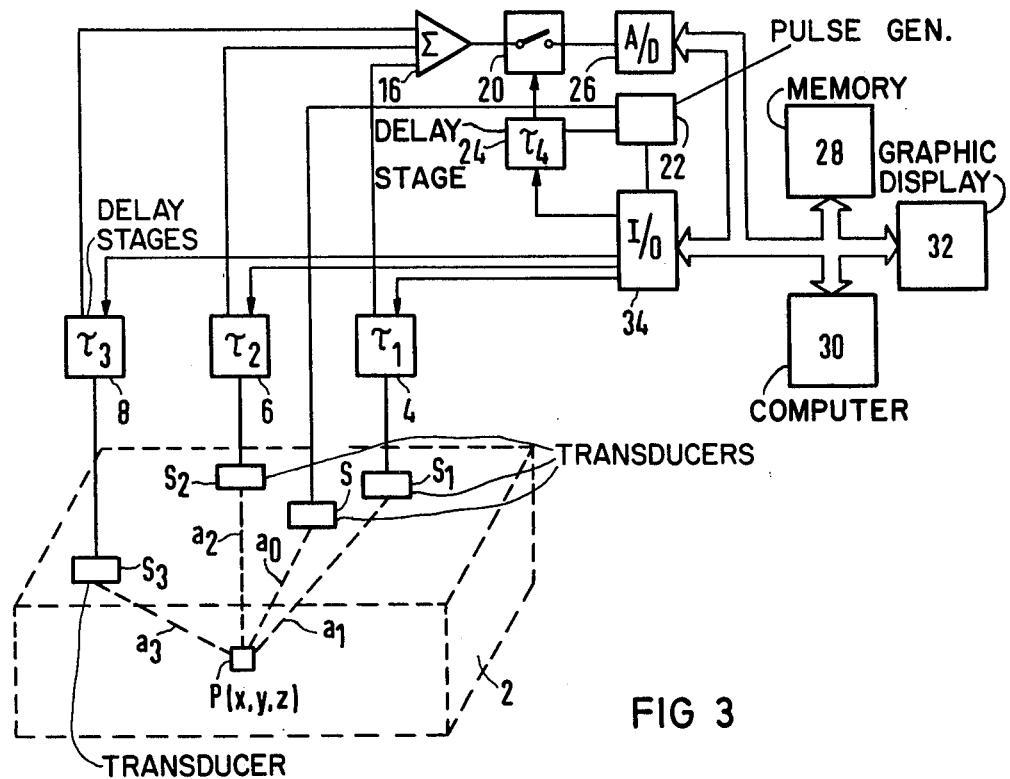
FIG. 3 is a block diagram of a special embodiment of an arrangement for implementing the method.
Figure 4:
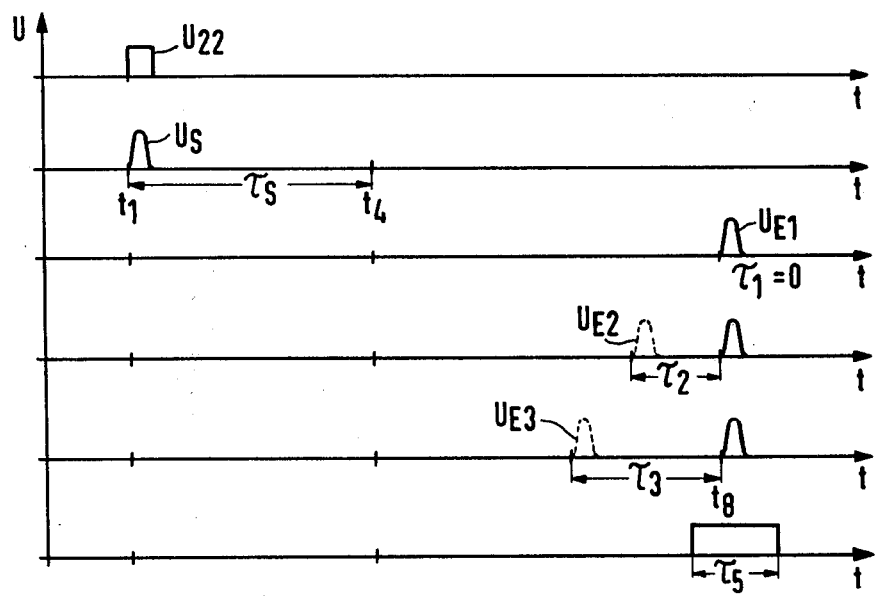
FIG. 4 is a diagram illustrating the operation of arrangement of FIG. 3.

In the arrangement according to FIG. 3, a special ultrasonic transducer with spherical characteristic is provided as the transmitter S, to which a transmitting pulse $U_{22}$ is fed directly from the pulse generator 22, as is illustrated in the diagram according to FIG. 4 in which the different pulses are plotted as a function as the time t. The pulse $U_{22}$ is set into the transmitter S without delay and triggers a transmitting pulse $U_S$ at the time $t_1$. The ultrasonic transducers $S_1$ to $S_3$ merely serve as receivers for the echo pulses reflected by the fault at point P. The transmitter S and the receiver $S_1$ to $S_3$ are arranged at a predetermined distance from each other on the surface of the workpiece 2. The ultrasound pulse delivered by the transmitter S travels through the distance $a_o$ in the workpiece 2 during the time $\tau_s$ to the point P and is reflected there at the time $t_4$. The echo signals require different predetermined times for travelling through the distances $a_3$, $a_2$ and $a_1$, according to the sound velocity in the workpiece 2. The echo signals $U_{E1}$, $U_{E2}$ and $U_{E3}$, transmitted by the receivers $S_1$ to $S_3$, are passed on by the delay stages 4, 6 and 8 with different delay times $\tau_1 = 0$ or $\tau_2$ or $\tau_3$ delayed in such a manner that they reach the summing amplifier 16 and therefore the gate 20, which is open during the time $\tau_5$, simultaneously at the time $t_8$. The opening of the gate 20 is accomplished via the delay stage 24 which is started by the pulse generator 22. The setting of the delay times of the electronic delay stages 4, 6 and 8 and 24 is accomplished by the computer 30 via the I/O interface 34.

The arrangement for implementing the method according to FIG. 3 has the advantage that with the separate transmitter S which serves only for introducing the transmitter pulse, a relatively large amount of energy can be radiated into the workpiece 2, i.e., an ultrasonic transducer which has a particularly high electromechanical efficiency can be used as a transmitter. The ultrasonic transducers now serving only as receivers $S_1$ to $S_3$ can then be designed specially for high sensitivity and can preferably consist of polyvinylidene fluoride $PVF_2$ or also of polyvinylidene chloride $VPC_2$ or polycarbonate.

For instance, a pulsed laser, especially a semiconductor laser can be provided as a transmitter S. As receivers, interferometers which operate according to the principle of the Michelson interferometer can also be provided. Furthermore, sector scanners may be provided as ultrasonic transducers.

In the embodiment of the reflector localization system according to FIG. 3 with the separate transmitter S, the deviation of the position of the transmitter S from the plane which is defined by the three contact points of the receivers $S_1$ to $S_3$, is measured and this deviation is set into the computer 30 to be taken into consideration when calculating its control signals.

The signals are superimposed in the summing amplifier. If one of the echo signals has only a relatively low amplitude due to the shape of the fault, for instance, a crack in the direction of one of the vectors $a_1$ to $a_3$ or with only a small inclination with respect to one of these vectors, then these different signal amplitudes are partly equalized by the summing in the amplifier 16, i.e. the fault anisotropy is approximately compensated. The open time of the gate 20 is chosen so that only a time interval which corresponds to the desired resolution is covered. A reflection of the insonification signals at the opposite surface of the workpiece or at faults which are located outside the insonified volume element, is picked upon only to the extent that the correct time conditions prevail by chance.

This picture background can further be reduced by requiring minimum amplitudes in the individual branches. This additional requirement can be realized as a double or triple coincidence circuit.

In implementing the present invention, the ultrasonic transducers $S_1$ to $S_3$ may, for example, be pulsed lasers type LEM 1/14 produced by Siemens. The electronic time delay stages 4, 6, and 8 may be, for example, LeCroy Research Instru. Type 2256A. If such arrangements are used, they take place not only of the time delays, but also of the digital to analog converter so that digital information will be fed from each of the three transducers to the computer. The computer may then perform the appropriate gating and summing functions in conventional fashion. In other words an internal timer in the computer will be used to take the place of the time delay stage 24 so as to take, in through I/O interface 34, only the echo data received at the proper time. Within the computer, this data will then be summed and stored. In this embodiment, the pulse generator will be incorporated within the type LEM 1/14 pulsed lasers. The computer, which includes a microprocessor 30, memory 28 and graphic display 32 may be a process computer PR 330 with a graphic display.

In the embodiment of FIG. 3, the pulse generator 22, and transmitter S may comprise, again, a Siemens type LEM 1/14 pulsed laser. The transducers $S_1$ to $S_3$ may be laser interferometers produced by PCL of Dorking, England. The remaining elements will be the same as in FIG. 1. Naturally, other well known elements may equally well be used.

Figure 5:
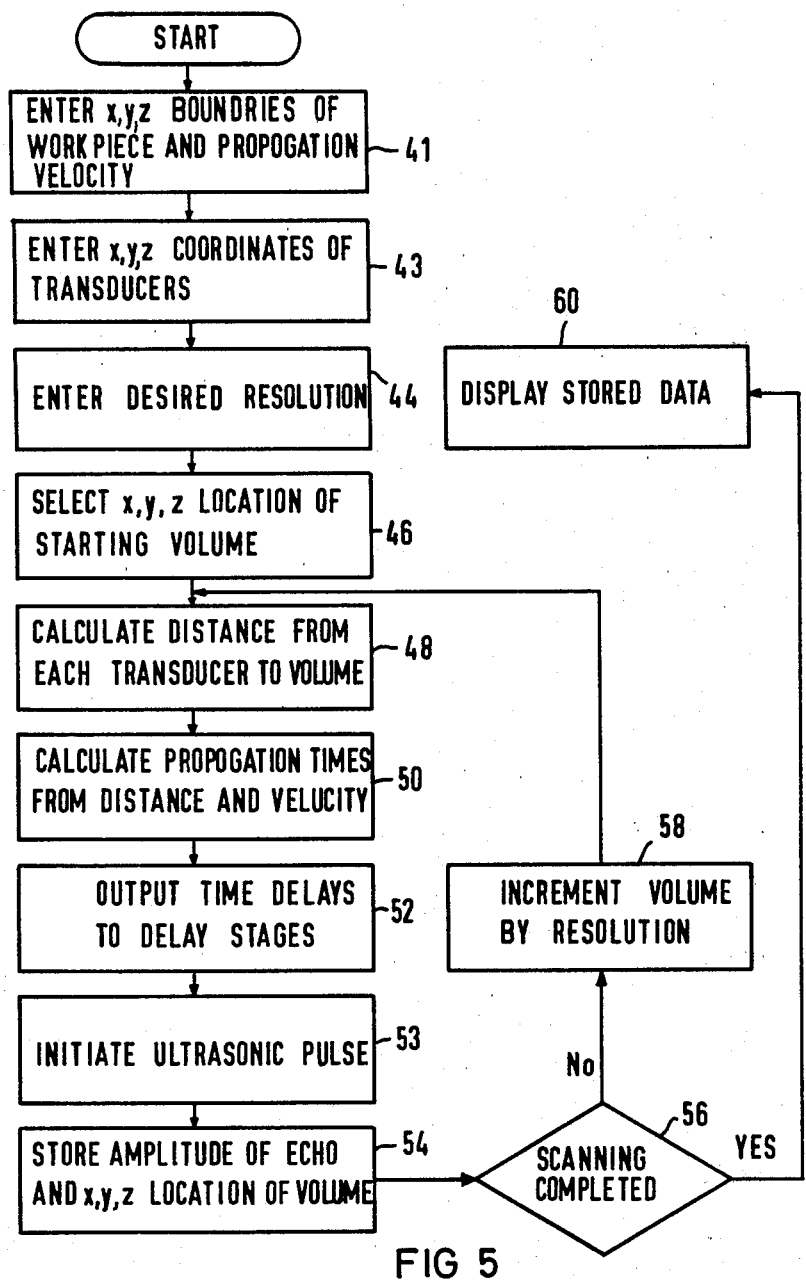
FIG. 5 is a flow diagram for the program of the computer of FIG. 3.

A flow diagram of the type of program which will be contained in the microprocessor 30 to implement the embodiment of FIG. 3 is set out in FIG. 5. In the first step 41, the x, y and z coordinates of the workpiece boundaries, i.e., the boundaries to be scanned, and the propagation velocity in the material under test are entered into the computer. Next, as shown by block 43, the x, y and z coordinates of the transducers S, $S_1$, $S_2$ and $S_3$ are entered. Next, according to block 44 the desired resolution is entered. As noted above, a coarse scan can be made first followed by a fine scan in the area of interest. Next, based on the boundary information set in, a starting point, for example, at a corner, may be selected. From the x, y, z location of the starting volume and the x, y, z location of the transducers, it is then possible, as shown by block 48, to calculate the distance from each transducer to the selected volume. Then, as shown by block 50, the propagation times from the volume to each of the transducers may be calculated using this distance and the velocity constant. This information is then used to provide digital outputs to the time delays 4, 6 and 8 along with the time delay 24. It is now possible to output the pulse, i.e., to trigger the pulse generator 22, which will supply a pulse to the transducer S and to the time delay 24. As explained above, if there is a fault in the selected volume, i.e., at point P of FIG. 3, echoes will then be transmitted back to the transducers $S_1$, $S_2$ and $S_3$. Because of the calculated time delays, the sum of these echoes will be gated through the analog gate 20 and the analog to digital converter 26 into the computer only during a window time corresponding to the calculated propagation times. As indicated by block 54, this echo data is then stored in the memory 28 along with the x, y, z location of the volume from which it was received. Next, the program enters a decision block 56 where it is determined whether or not scanning has been completed. If it has not, as indicated by block 58, the volume is incremented by the selected resolution and the program loops back to block 48. The steps 48, 50, 52, 53, 54, 56 and 58 are repeated with the echo and coordinate information stored for each increment of volume until the whole volume has been scanned. When scanning is completed, as indicated by a yes answer from the decision block 56, the stored data is displayed in conventional fashion on the graphics display 32 as indicated by block 60.

If one uses the type of apparatus, outline above, where there is no external summing amplifier, gate and time delay 24, additional steps are required in the program. Prior to the output of a pulse in block 53, an internal timer will be preset with a value corresponding to the maximum propagation delay, i.e., the time for the pulse to be transmitted from the transmitter S, reflected at the fault at location P, and the echo received by the furthest receiving transducer. At the time of the output pulse, as shown by block 53, this timer is started. When the timer times out, the three analog to digital converters associated with the three time delays will be enabled for a predetermined period of time proportional to the desired resolution and the echo amplitudes from the three received in the computer. A further step of adding the three received echo amplitudes will then ensue, followed by step 54 of storing the summed amplitude and the x, y, z coordinates. In all other respects, the program will be as outlined by the flow diagram of FIG. 4.

What is claimed is:

1. In a method for nondestructive material testing with ultrasound pulses which are introduced into a workpiece under test and are reflected by a fault, the position of which is derived from the propagation time of the ultrasound pulses and the echo pulses, the improvement comprising picking up the ultrasonic echo pulse reflected in the workpiece at the fault at three different points of the surface, said three points spaced from each other in such a manner so as to define only one single plane; electronically adding the electronic echo pulses in phase, each with a delay depending on its respective travel time; and feeding the resulting sum to an electronic memory through an electronic time window.

2. The method according to claim 1, and further including converting the echo pulses into digital signals and displaying said signals on a picture screen.

3. The method according to claim 1, comprising transmitting ultrasound pulses to each point being scanned from three points at the surface arranged at predetermined distances from each other, at a time spacing such that they reach said point and are reflected by any fault thereat simultaneously, using said same three points as echo signal pickup points, and selecting the delays of the echo pulses received at the points to be equal to the time spacings of the transmitted ultrasound pulses.

4. The method according to claim 3, and further comprising first scanning large volume elements of the workpiece by successively transmitting to points at larger distance from each other by choosing the time spacings of the ultrasound pulses, the time delays of the echo pulses and the length of said time window, and, as soon as a fault is determined, further scanning the vicinity of said fault at higher resolution.

5. Apparatus for nondestructive material testing with ultrasound pulses which are introduced into a workpiece under test and are reflected by a fault, the position of which is derived from the propagation time of the ultrasound pulses and the echo pulses, comprising:
  (a) an ultrasonic transmitter disposed on the surface of the workpiece;
  (b) three ultrasonic receivers disposed at predetermined distances from each other on the surface of the workpiece, said three receivers lying in and defining only a single plane;
  (c) an electronic pulse generator coupled to supply pulses to said transmitter;
  (d) a summing amplifier;
  (e) respective electronic delay stages coupling said receivers to said summing amplifier;
  (f) an analog gate having an enabling input and an input from the output of said amplifier; and
  (g) a further electronic delay stage coupling the output of said pulse generator to said enabling input to generate an electronic time window.

6. Apparatus according to claim 5, comprising three ultrasonic transducers disposed at a predetermined distance from each other on the surface of the workpiece, said transducers acting both as transmitters for ultrasound pulses and as receivers for echo pulses; and respective double throw switches for coupling the delay stages associated to the ultrasonic transducers first to the pulse generator then to said amplifier.

7. Apparatus according to claim 5 and further including an electronic computer for controlling said electronic delay stages.

8. Apparatus according to claim 5 wherein a pulsed laser is provided as the transmitter.

9. Apparatus according to claim 5 wherein Michelson interferometers are provided as the receivers.

10. Apparatus according to claim 5 wherein piezo converters of the polyvinylidene fluoride foil type are provided as the receivers.

11. Apparatus according to claim 5 wherein said ultrasonic transducers comprise sector scanners.

* * * * *